(12) United States Patent
Frankel

(10) Patent No.: US 7,483,766 B1
(45) Date of Patent: Jan. 27, 2009

(54) SYSTEM AND METHOD FOR PRESCRIBING AND CONVEYING PHARMACEUTICALS WITHIN THE PREMISES OF A HEALTHCARE PROVIDER

(76) Inventor: Mark E. Frankel, 107 Beaumont Pl., Lower Gwynedd, PA (US) 19002

( * ) Notice: Subject to any disclaimer, the term of this patent is extended or adjusted under 35 U.S.C. 154(b) by 62 days.

(21) Appl. No.: 11/476,220

(22) Filed: Jun. 27, 2006

(51) Int. Cl.
G06F 17/00 (2006.01)

(52) U.S. Cl. ............... 700/237; 700/235; 700/240; 700/241

(58) Field of Classification Search .......... 700/237, 700/241, 236
See application file for complete search history.

(56) References Cited

U.S. PATENT DOCUMENTS

| | | | | |
|---|---|---|---|---|
| 4,847,764 | A * | 7/1989 | Halvorson | 700/236 |
| 5,014,875 | A * | 5/1991 | McLaughlin et al. | 700/236 |
| 5,431,299 | A * | 7/1995 | Brewer et al. | 221/2 |
| 5,797,515 | A | 8/1998 | Liff et al. | 221/2 |
| 5,883,370 | A | 3/1999 | Walker et al. | 235/375 |
| 6,067,524 | A | 5/2000 | Byerly et al. | 705/3 |
| 6,109,774 | A * | 8/2000 | Holmes et al. | 700/237 |
| 6,219,587 | B1 * | 4/2001 | Ahlin et al. | 700/233 |
| 6,564,121 | B1 * | 5/2003 | Wallace et al. | 700/237 |
| 6,636,780 | B1 * | 10/2003 | Haitin et al. | 700/236 |

* cited by examiner

Primary Examiner—Gene Crawford
Assistant Examiner—Timothy R Waggoner
(74) Attorney, Agent, or Firm—LaMorte & Associates (57) ABSTRACT

A system and method of prescribing and conveying regulated pharmaceuticals. Prepackaged pharmaceuticals are kept in a vending machine. Upon the completion of a patient's diagnosis, a physician may prescribe a regulated pharmaceutical. The physician enters the prescription into a terminal. The prescription is read by a central processing unit that controls the vending machine. The central processing unit identifies the location of the pharmaceutical in the vending machine and awaits a proper vending code. Once a physician enters a prescription into the system, the physician hands the patient an electronic key card. The key card is encoded with the vending code needed to activate the vending machine. The patient carries the key card to the vending machine. If the code on the key card matches the prescription code previously entered by a physician, the vending machine vends the prepackaged pharmaceutical.

16 Claims, 5 Drawing Sheets

SYSTEM AND METHOD FOR PRESCRIBING AND CONVEYING PHARMACEUTICALS WITHIN THE PREMISES OF A HEALTHCARE PROVIDER

RELATED APPLICATIONS

This application claims the priority of provisional Patent Application No. 60/175,001, filed Jun. 30, 2005, entitled Method And System For Distribution Of Regulated Substances And Materials.

BACKGROUND OF THE INVENTION

1. Field of the Invention

In general, the present invention relates to systems and methods that enable a healthcare provider to electronically create a prescription. The present invention also relates to systems and methods that are used to convey pharmaceuticals in an automated manner. More particularly, the present invention relates to the overall integration of a prescription creation and conveying system that safeguards against prescription fraud and preparation error.

2. Prior Art Description

When a person is sick, they commonly use the services of a professional healthcare provider. In the standard course of operation, healthcare providers regularly examine and diagnose patients in their offices. Typically, a sick patient will meet with the healthcare provider in his/her office. The healthcare provider will diagnose the illness and suggest a course of action to treat the illness. Often, the suggested course of action involves the taking of a medication. If the selected medication is a controlled pharmaceutical, the healthcare provider writes a prescription for the patient. The patient takes the prescription to a pharmacy, wherein a pharmacist fills the prescription. As such, sick patients must proceed through a two-step process before they receive medication for their ailment. The patient must first visit with a healthcare provider to obtain a prescription. The patient must then visit with a pharmacist to have the prescription filled.

The two-step process of obtaining medication for an ailment presents many problems for a patient. The obvious problem is one of inconvenience. It takes time to visit both a physician's office and a pharmacy. It also takes time for a pharmacy to fill a prescription. Consequently, there can be a delay of many hours between when a physician hands a patient a prescription for a medication and the time that the patient has that medication in hand.

Furthermore, just because a patient is given a prescription does not mean that the patient will fill the prescription. A patient may believe that the physician is wrong in their diagnosis. Alternatively, a patient may procrastinate, hoping the aliment will pass without medication. A patient may also lose the prescription, forget about the prescription or purposely not fill the prescription for a variety of financial, religious and/or personal reasons.

The other problems associated with the two-step process of receiving mediations are much less obvious, but far more important. When a patient arrives at a pharmacy, the patient must hand the pharmacist the prescription. The pharmacist must assume that the prescription is proper for both the patient and the illness being treated. In other words, the pharmacist must assume that the doctor did not make any error in writing the prescription and has handed the correct prescription to the correct patient. The pharmacist must then decipher the physician's handwriting and understand what has been prescribed in what amounts. If the pharmacist misreads the prescription in any way, the prescription will be incorrectly prepared.

Assuming the physician did not err in issuing the prescription and the pharmacist did not err in reading the prescription, the pharmacist must then properly fill the prescription and label the prescription. If the pharmacist errs in either filling or labeling the prescription, the patient may take the wrong medication or may take the right medication, but the wrong dosage. The patient may also be given the proper medication, in the proper dosage, but with incorrect dosing instructions.

Finally, once a prescription is prepared and labeled, it must be given to the correct patient. Most pharmacies do not ask to see identification from patients. The prescription is often just handed to the first person who asks for the prescription and pays for the prescription.

Most patients assume that the prescription given to them at the pharmacy is correct. If a patient is handed the wrong prescription, there is a good chance that the patient will take that medication without ever reading the label on the bottle.

In addition to all the problems that may accidentally occur in traditional systems, many people also attempt fraud to acquire pharmaceutical prescriptions. Such people take advantage of the many problems of the system to forge, falsify, and steal pharmaceuticals.

It will therefore be understood that in order for a person to properly receive a prescription, there must be no human error in writing, handling, filling, labeling and delivering the prescription. Although the system works correctly the vast majority of the time, human error will always be present. Thousands of such errors occur every year. These errors could result, either directly or indirectly, in deaths, permanent injury, illness, harmful drug interactions and untreated disease. This creates liabilities to pharmacists and doctors resulting in increased healthcare costs for everyone.

Despite training and safety protocols, the only way to reduce human error is to minimize the points in the system where human error can occur. To prevent physicians from writing illegible prescriptions, many electronic prescription systems have been created that electronically transmit prescriptions to pharmacies. Such prior art systems are exemplified by U.S. Pat. No. 6,067,524 to Byerly, entitled Method And System For Automatically Generating Advisory Information For Pharmacy Patients Along With Normally Transmitted Data; and U.S. Pat. No. 5,883,370 to Walker, entitled Automated Method For Filling Drug Prescriptions.

Perhaps the most common place where errors occur is in the filling, labeling and delivery of the prescription by the pharmacist. One way to minimize human error in these processes is to create automated machines that convey prepackaged pharmaceuticals.

There are many ways to convey prepackaged goods to the public using automation. The most common way to convey prepackaged good is through the use of vending machines. Vending machines can vend any product that is placed into the vending machines, including prepackaged pharmaceuticals. Vending machines can also be left accessible to the public at all times, thereby enabling a person to fill a prescription at their own convenience. Vending machines specifically configured to vend prescription pharmaceuticals are exemplified by U.S. Pat. No. 5,797,515, to Liff, entitled Method For Controlling A Drug Dispensing System.

Replacing a human pharmacist with an automated vending machine presents its own set of problems. First, the vending machine must be manually filled with the proper medications. Human error may cause the vending machine to be incorrectly filled. Furthermore, as most everyone has experienced, vending machines do not always vend properly. Merchandise gets jammed. Sometimes nothing vends from the machine, sometimes two products accidentally vend from the machine.

A need therefore exists for an improved prescription preparation and conveying system that eliminates as much human error as possible by using automating processes. A need also exists for an improved automated conveying system for prescription pharmaceuticals that safeguards against many prevalent errors that are inherent in prior art automated systems. These needs are met by the present invention as described and claimed below.

SUMMARY OF THE INVENTION

The present invention is a system and method of prescribing and conveying regulated pharmaceuticals within the confines of a physician's office. A stock of prepackaged units of use is provided. A prepackaged unit-of-use is a sealed bottle, jar, vial or package that contains a prescribed course of medication. The stock of prepackaged units of use are kept in a vending machine. The activation of the vending machine is controlled by a central processing unit. The system also contains a data reading unit that is located in or near the vending machine.

Upon the completion of a patient's diagnosis, a physician may prescribe a regulated pharmaceutical. If the pharmaceutical is present within the vending machine, the physician enters the prescription into a terminal. The prescription is read by the central processing unit that controls the vending machine. The central processing unit identifies the location of the pharmaceutical in the vending machine and awaits a proper vending code.

In the preferred embodiment of the present invention, the physician hands the patient an electronic key card. The key card is encoded with the vending code needed to activate the vending machine. The patient carries the key card to the vending machine. The key card is read by the data reading unit. If the code on the key card matches the prescription code previously entered by a physician, the vending machine vends the prepackaged unit-of-use.

Through the use of sensors and label codes, the system verifies that the prepackaged unit-of-use has correctly vended from the machine and that the prepackaged unit-of-use is correct.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Although the present invention system and method can be used to convey controlled materials other than pharmaceuticals, the present invention is particularly well suited for use in the prescribing and conveying of prescription pharmaceuticals. Accordingly, the present invention system and method is described for use in conveying prescription pharmaceuticals in order to set forth the best mode contemplated for the invention.

Figure 1:
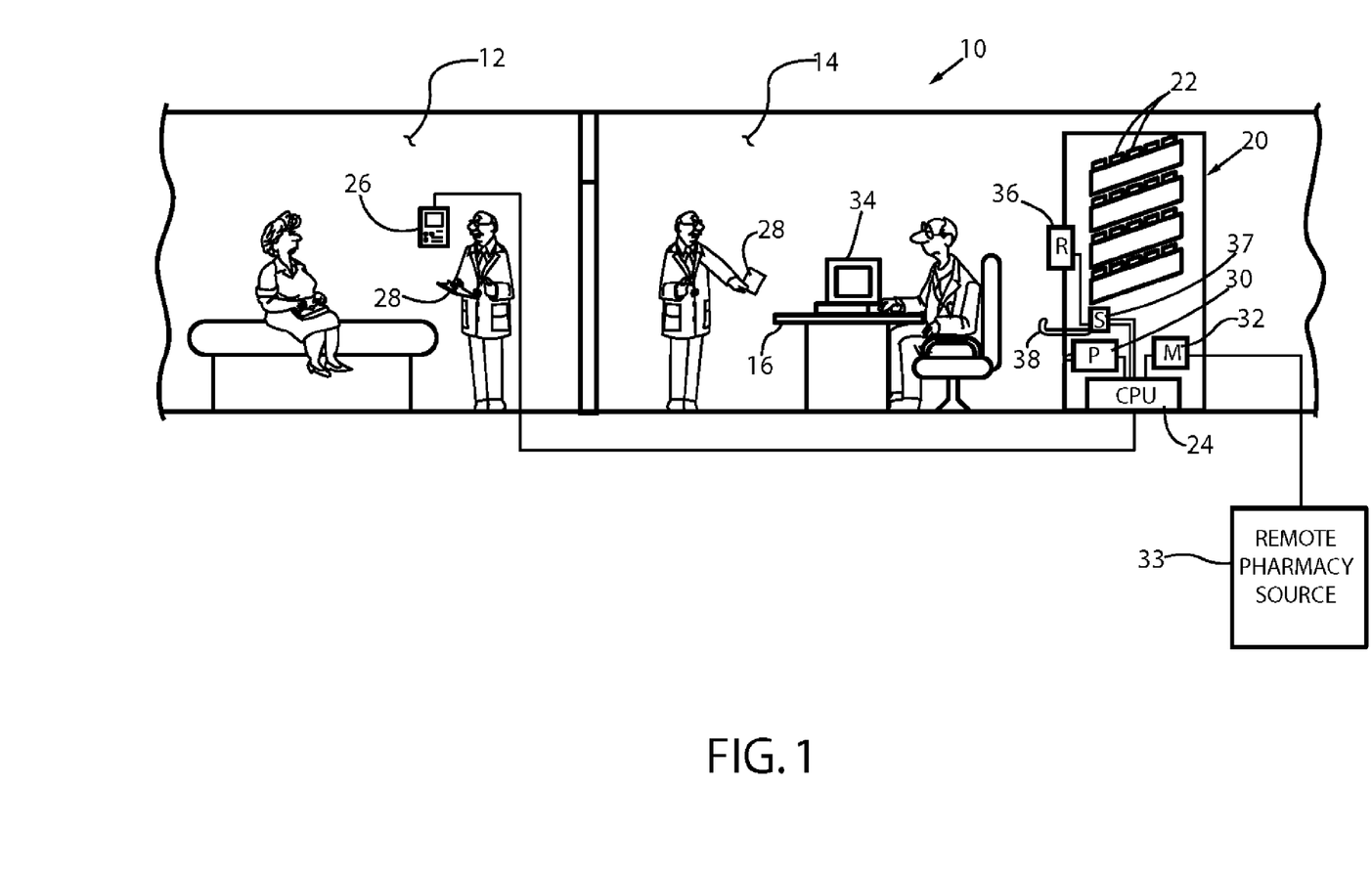
FIG. 1 is an exemplary schematic of a physician's office containing the present invention system.

Referring to FIG. 1, a schematic of a physician's office 10 is shown that contains the present invention system. As is typical, the physician's office 10 includes an examination room 12 and an office area 14. The examination room 12 is the room where physicians physically examine patients. The office area 14 typically is a restricted area that is only used by office personnel. The office area 14 usually has a countertop 16 that separates the office area 14 from public areas used by the coming and going patients.

The present invention system utilizes a custom vending machine 20 to store prepackaged units of use. A unit-of-use is a bottle, jar, vial, tube, syringe, package or other receptacle that is prefilled with pharmaceutical in a volume large enough to complete a course of treatment. The vending machine 20 is preferably kept in the restricted office area 14. However, the vending machine 20 may be present in public areas for direct access by patients.

The vending machine 20 contains a stock of prepackaged units of use 22. The prepackaged units of use 22 kept in the vending machine 20 depend upon the type of physician's office. In a pediatric physician's office, the vending machine 20 might, among other things, contain various antibiotics in dosages suitable for children of different weights and ages. In a geriatric physician's office, the vending machine might contain, among other things, prepackaged units of use for arthritis and hypertension. It will therefore be understood that the vending machine 20 will be stocked with the prepackaged units of use 22 that are most typically prescribed by the physicians in that office.

The vending machine 20 contains a central processing unit 24. The central processing unit 24 controls the vending mechanisms of the vending machine 20. As will later be explained, the central processing unit 24 also keeps track of the stock inventory carried and conveyed by the vending machine 20.

A data input terminal 26 is provided. Although the data input terminal 26 can be located anywhere, it is preferred that each of the examination rooms 12 be provided with a data input terminal 26. The data input terminal 26 can be a panel that is mounted to a wall, a tabletop computer terminal or a portable handheld device. Each of the data input terminals 26 are coupled to the central processing unit 24 using either a hard wire or radio frequency network.

Each of the data input terminals 26 can only be activated by an authorized physician from that office. The data input terminal 26 may be activated by the physical input of an access code or password. The data input terminal 26 may also be activated by swiping an identification card or providing some biometric data, such as a fingerprint. However, in the exemplary embodiment, the data input terminal 26 is activated by a radio frequency identification (RFID) tag that is carried by the physician. In this manner, the electronic input interface will automatically activate as the physician approaches that device.

The data input terminal 26 contains a screen. Once activated, the physician can enter a prescription for a pharmaceutical. The number of prepackaged units of use 22 held within the vending machine 20 are limited by the capacity of the vending machine 20. Thus, the vending machine 20 is filled with a selection chosen by the health care professionals of that office that are best suited for the patients served by that practice. The selections offered by the vending machine 20 can be presented to the physician on the data input terminal 26 in the form of a selection menu. The physician therefore needs only select one of the menu choices to complete a prescription. However, the data input terminal 26 also enables a physician to custom enter a prescription for any pharmaceutical, even if that pharmaceutical is not carried by the vending machine 20. If a particular pharmaceutical is not contained in the vending machine 20, a printed prescription will print for the patient to take to a pharmacy in the traditional manner.

Key card sets are provided. Each of the key card sets contains two key cards 28 that are electronically matched. The key cards 28 are preferably kept secure prior to use. The key cards 28 are therefore held by the physician or are kept in a secure manner near the data input terminal 26 in the examination room 12. Each of the key cards 28 in each key card set contain a vending code. In the preferred embodiment, the vending code is contained in an RFID tag that is present on each of the key cards 28. The data input terminal 26 can therefore passively read the vending code from the key card 28 just by holding the key card 28 proximate the data input terminal 26 when prompted by the data input terminal.

It will be understood that although an RFID tag is preferred, the vending code can be read in other manners. For instance, the key card 28 may contain a magnetic strip, barcode, digital data storage chip, magnetic storage disk, optical storage disk or other readable data sequence that can read to the data input terminal 26. Alternatively, the key card 28 may just contain a printed vending code that can be manually entered into the data input terminal 26.

Regardless to the method of data transfer, what is of importance is that the vending code from a key card 28 is read by the data input terminal 26. That vending code becomes associated with the prescription data that was just entered into the data input terminal.

Once prescription data and a corresponding vending code are entered into the data input terminal 26, both the prescription data and the vending code are automatically forwarded to the central processing unit 24 in the vending machine 20.

The central processing unit 24 in the vending machine 20 is coupled to a printer 30. The printer 30 can be a tabletop printer. However, in the shown embodiment, the printer 30 is contained within the structure of the vending machine 20.

A modem 32 is coupled to the central processing unit 24. The modem 32 enables the central processing unit 24 to communicate with a remote pharmacy source 33, via some existing telecommunications network. In this manner, the central processing unit 24 can keep the remote pharmacy source 33 aware of the inventory and age of the prepackaged units of use 22 within the vending machine 20. Periodically, or as needed, the remote pharmacy source 33 will send a person to restock, replace or remove the prepackaged units of use 22 from the vending machine 20.

The central processing unit 24 also communicates with the physician's electronic medical record system, via an office computer 34. In this manner, when a prescription is written for a particular patient, that information may be saved to the medical records of that patient.

Having described an exemplary physical layout of the present invention system, the system's method of operation can now be described. Referring to FIG. 1 in conjunction with FIG. 2, it can be seen that the present invention system is contained within a physician's office 10 or other healthcare facility, such as a hospital. A patient is taken to an examination room 12, wherein the patient is examined by a physician. See Block 40. The physician diagnoses the cause of illness in the patient and conceives of a treatment. See Block 42. If the treatment includes the need for a prescription, the physician activates the data input terminal 26. See Block 44. Using the data input terminal 26, the physician enters a prescription. See Block 46. The physician also takes a key card set. The physician reads the vending code from one key card 28 into the data input interface so that the vending code becomes associated with the prescription data. See Block 48. The second key card 28 is handed to the patient for later use at the vending machine 20. See Block 50.

Figure 2:
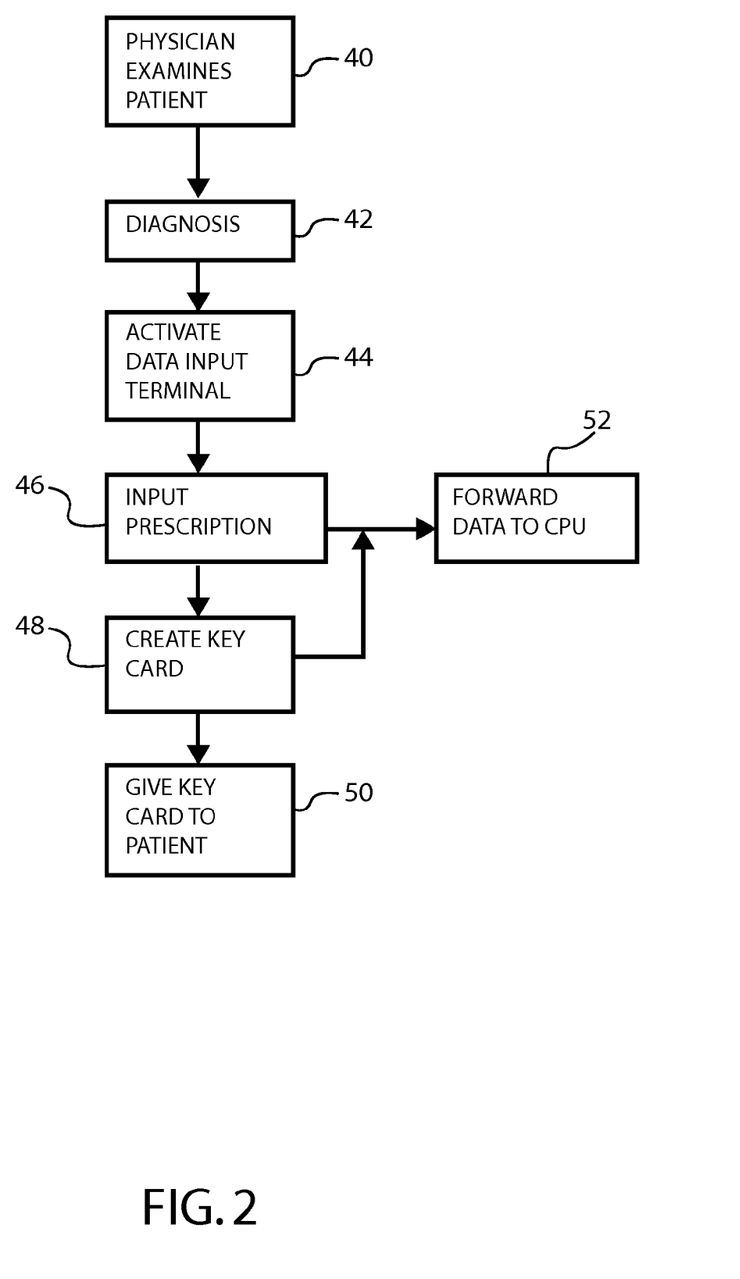
FIG. 2 is a block diagram showing another part of the methodology used by the present invention system.

The prescription information and vending code that were entered into the data input terminal 26 are forwarded to the central processing unit 24. See Block 52.

Figure 3:
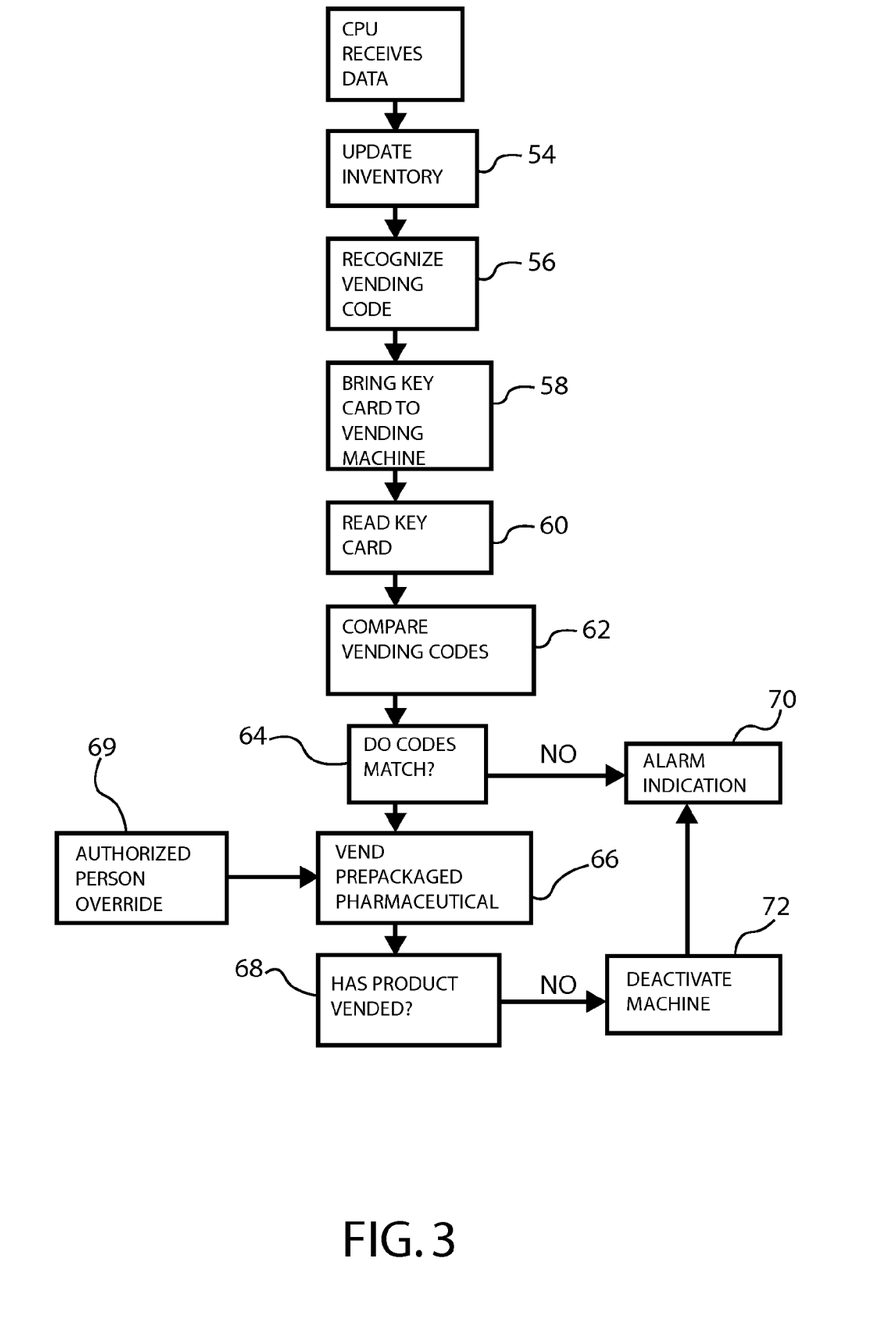
FIG. 3 is a block diagram showing yet another part of the methodology used by the present invention system.

Referring to FIG. 3 in conjunction with FIG. 1, it will be understood that once the central processing unit 24 receives prescription data from the data input terminal 26, it deducts the prescription from the inventory of the vending machine 20, even though the vending machine 20 has not yielded the prescription. The central processing unit 24 immediately updates inventory information, as is indicated by Block 54. In this manner, if another physician in another office were to prescribe that same medication, the physician would know if that medication were available within the vending machine 20.

In the illustrated embodiment, the vending machine 20 contains a data reading unit 36. Such a location is exemplary, and it will be understood that the data reading unit can be remote from vending machine 20 provided it remains in communication with the vending machine 20. The data reading unit 36 can read the key card 28 of the patient. The type of data reading unit 36 depends upon the type of key card 28 being used. For example, if the key card 28 is a card with a magnetic strip, the data reading unit 36 is a card swipe reader. In the preferred embodiment, the key card 28 contains an RFID tag. As such, the data reading unit 26 would be an RFID reader. Regardless, what is of importance is that the data reading unit 36 is capable of reading data from the key card 28.

A patient brings the key card 28 to the vending machine 20 or hands it to an office worker who brings it to the vending machine 20. See Block 58. The key card 28 is then read by the data reading unit 36. See Block 60. Once the key card 28 is read, the central processing unit 24 matches the vending code from the key card 28 to the vending code that was previously received with the prescription data from the data input terminal 26. See Block 62. If the vending codes match, the central processing unit 24 then enables the vending machine 20 and vends the appropriate prepackaged unit-of-use 22. See Blocks 64 and 66.

It will therefore be understood that the vending machine 20 does not have selection buttons in the manner of a traditional vending machine. Rather, the vending machine 20 automatically vends only after the key card 28 is read by the vending machine 20 and compared to a vending code. The data in the vending code controls which of the prepackaged pharmaceuticals will be vended when the vending machine 20 is activated. The chance of an incorrect selection being made by human error is therefore eliminated.

The need for the proper key card can be circumvented by an authorized person. Using a master key card, or the key card that was kept by the physician, a physician or a member of the physician's staff can cause the vending machine 20 to vend. See Block 69. Alternatively, a physician can over-ride the requirement of a key card when the physician enters a prescription into the system. In this manner, a prepackaged unit-of-use 22 can be retrieved from the vending machine 22 for a patient who is homebound or otherwise unable to come to the office.

Since the vending machine 20 is automatically activated by the vending code on a key card 28, there is no concern about a person pressing the wrong selection buttons and/or receiving the wrong medication. Accordingly, the only way a patient can receive the incorrect prescription is if the vending machine 20 is filled incorrectly or fails to vend properly.

A sensor 37 can be placed in the receiving tray 38 of the vending machine 20. The sensor 37 is coupled to the central processing unit 24. As is indicated by Block 68, the sensor 37 detects whether or not a prepackaged pharmaceutical 22 has been conveyed into the receiving tray 38 after the vending machine 20 has vended. If no prepackaged unit-of-use 22 is detected, it can be assumed that the prepackaged unit-of-use 22 got stuck in the vending machine 22 or the vending machine 22 was not filled properly and vended a blank space. If the central processing unit 24 detects any such vending error, the central processing unit 24 can alert the office staff and alert the operator of the vending machine. See Block 70. The vending machine 20 will also automatically deactivate to ensure that a subsequent patient does not receive the prepackaged unit-of-use that may be only temporarily stuck within the vending machine. See Block 72.

The printer 30 is connected to the central processing unit 24. The printer 30 can be located within the vending machine 20 or at some position close to the vending machine 20. Every time the vending machine 20 is activated by the central processing unit 24, the central processing unit 24 sends a print job to the printer. The print job corresponds to the pharmaceutical being conveyed. The print job, once printed, provides information about the pharmaceutical, such as its instructions for use and possible side effects. The printing also contains identification information that helps ensure that the pharmaceutical that was vended was the pharmaceutical that was intended.

Figure 4:
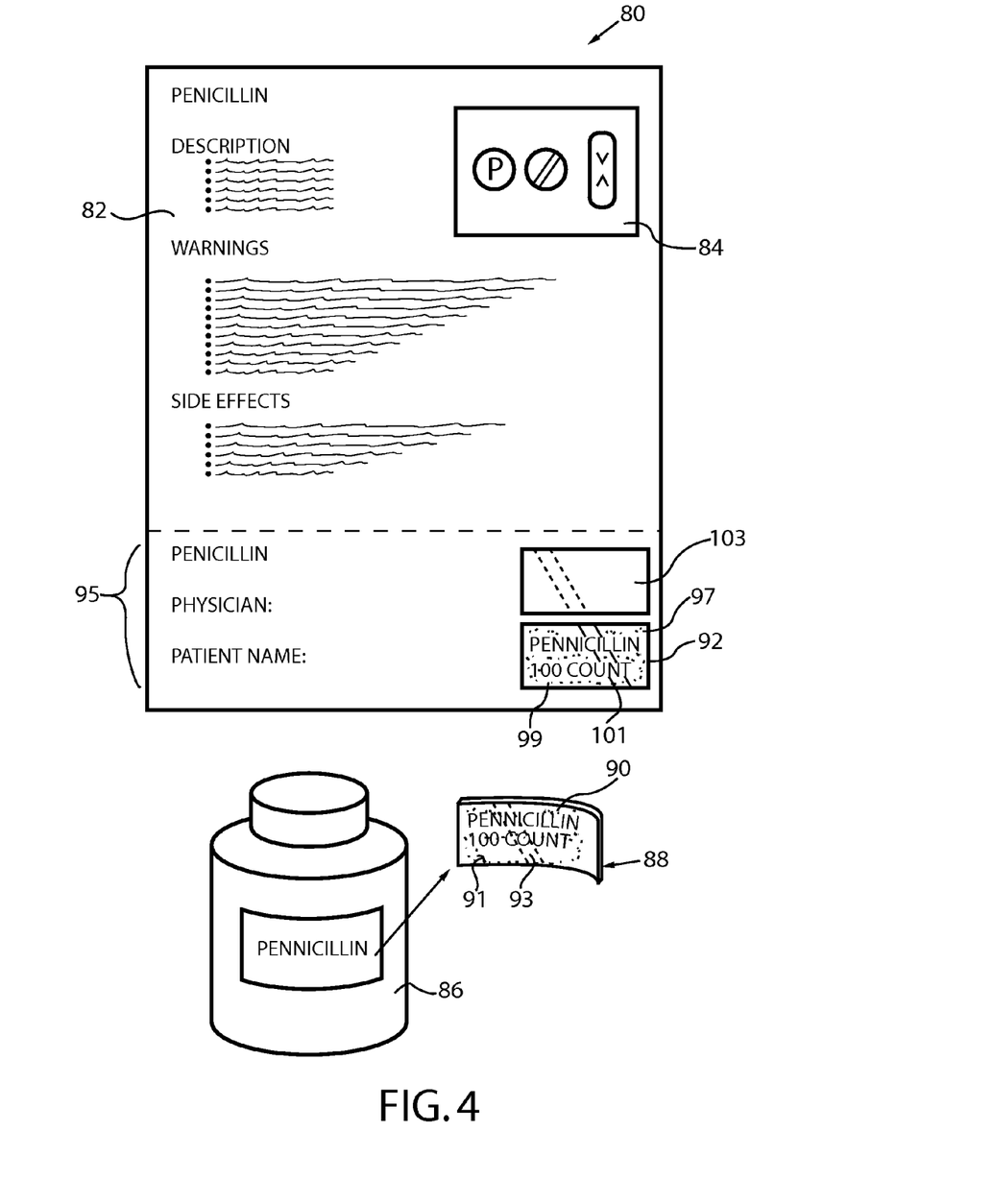
FIG. 4 shows an exemplary printout created by the present invention system and shown with a prepackaged pharmaceutical container.

Referring to FIG. 4, an exemplary embodiment of a printout 80 is shown. The printout 80 has an information section 82 that preferably contains some the warnings and technical information about the pharmaceutical being conveyed. The printout 80 also has a picture section 84 that shows color pictures of the pharmaceutical being conveyed. More than one picture may be provided if the pharmaceutical is manufactured by more than one company and comes in different sizes, shapes and/or colors.

A prepackaged pharmaceutical container 86 is also shown in FIG. 4. When such a prepackaged pharmaceutical container 86 vends from the vending machine, it contains a removable label 88. The removable label 88 identifies the pharmaceutical being in the prepackaged container 86 and also provides a code pattern 90 that is unique to that type of prepackaged unit-of-use. The code pattern 90 can be a color code, a numerical code, graphic code or any other visual code. In the exemplary embodiment, the code pattern consists of a color field 91 and an alignment strip 93.

The printout contains a tear-away section 95. A label image 92 is printed onto the tear-away section 95. The label image 92 contains a code pattern 97 that corresponds to the code pattern 90 on the removable label 88 from the prepackaged container 86. The label image 92 also contains a color field 99 and an alignment strip 101.

A label target 103 is printed either immediately above or below the label image 92. The label target 103 shows a person where to place the removable label 88 from the prepackaged container 86.

The removable label 88 is peeled off of the prepackaged container 86 and is applied over the label target 103. Once in this position, the color field 91 of the removable label 88 should be the same color as the color field 99 of the label image 92. Furthermore, the alignment strip 93 of the removable label 88 should align with the alignment strip 101 on the label image 92.

By comparing the removable label 88 to the label image 88, two goals are achieved. First, by checking if the code patterns 90, 97 match, it can be seen that the proper prepackaged pharmaceutical container 86 was vended from the vending machine 20. This safeguards against any human error that may have occurred during the filling of the vending machine 20. Second, the tear-away section 95 of the printout is removed and kept by the office staff, thereby providing a permanent record of what was vended from the vending machine 20.

The vending machine 20 is not an ordinary vending machine in the sense that it does not vend for money and it is not a self-contained system. Rather, the vending machine 20 is used as the conveying mechanism for a larger system that is integrated throughout the physician's office.

Figure 5:
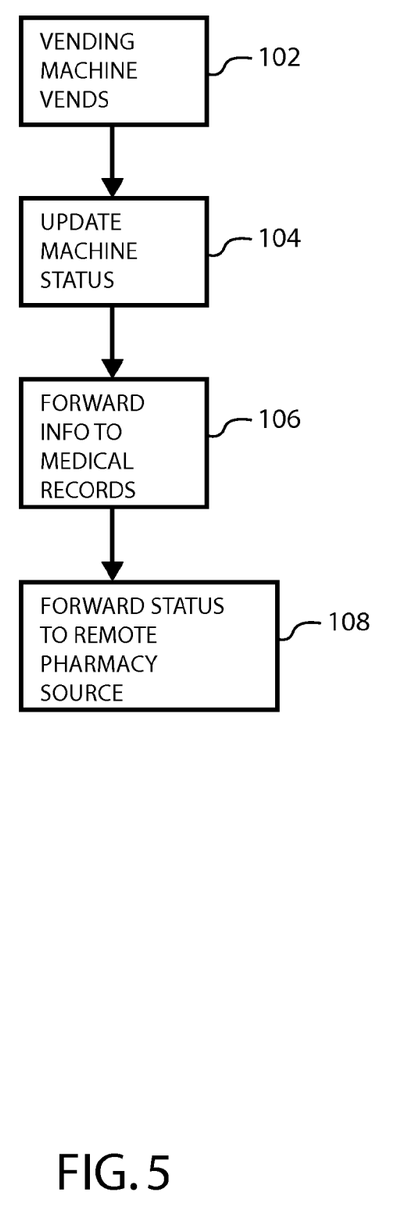
FIG. 5 is a block diagram showing yet another part of the methodology used by the present invention system.

Referring to FIG. 5 in conjunction with FIG. 1, it will be understood that as the vending machine 20 vends, the central processing unit 24 updates the status of the vending machine 20. See Blocks 100 and 102. Information about what was vended and for whom is communicated to the medical record software being run by the computer network in the physician's office. See Block 104. In this manner, a patient's records are automatically updated with the prescription ordered by the physician and the medication that was conveyed.

The central processing unit 24 also forwards update information to the remote pharmacy source 33 who is responsible for filling and maintaining the vending machine 20. In this manner, the remote pharmacy source 33 can periodically come to fill the vending machine 20 before the vending machine 20 ever runs out of a particular type of pharmaceutical.

It will be understood that the embodiment of the present invention system that is illustrated and described is merely exemplary and that a person skilled in the art can make many variations to the system. Individual system parts, such as the key card, data input terminal, and data reading unit come in many different types. All variations of these components are intended to be included within the scope of the invention. Furthermore, the term vending machine is being used in it broadest sense. The vending machine is intended to include all storage devices, including locked storage chests, that can only be accessed upon the activation of some conveying mechanism. All such variations, modifications and alternate embodiments are intended to be included within the scope of the present invention as set forth by the claims.

What is claimed is:

1. A method of prescribing and conveying regulated pharmaceuticals, comprising the steps of:
    providing a central processing unit;
    providing a stock of pharmaceuticals that are prepackaged as units of use, wherein each unit of use is a sealed container that contains a single pharmaceutical type in a quantity equal to an average course of treatment of said pharmaceutical type for a particular patient type;
    providing a vending machine that is controlled by said central processing unit, said vending machine storing said stock of pharmaceuticals therein, wherein each of said units of use can be independently vended and automatically dispensed from said vending machine upon the activation of said vending machine;
    providing a data reading unit proximate said vending machine that electronically communicates with said central processing unit;

providing a data input terminal that communicates with said central processing unit and is remote from said vending machine;

entering prescription data into said data input terminal, wherein said prescription data is forwarded to said central processing unit, and wherein said prescription data identifies one of said units of use within said vending machine;

assigning a first vending code to said prescription data;

providing a portable data storage medium containing a second vending code that is matched to said first vending code;

reading said second vending code from said portable storage medium with said data reading unit;

activating said vending machine if said second vending code read from said portable storage medium is matched to said first vending code by said central processing unit;

vending one of said units of use identified by said prescription data assigned to said first vending code; and printing a printout each time one of said units of use vends from said vending machine, wherein each said printout contains a label image.

2. The method according to claim 1, further including the step of having said central processing unit track said stock of said pharmaceuticals stored within said vending machine.

3. The method according to claim 2, further including the step of indicating on said data input terminal when said stock of said pharmaceuticals is at least partially exhausted.

4. The method according to claim 1, further including the step of providing a printer that is controlled by said central processing unit.

5. The method according to claim 1, wherein each of said units of use contains a removable label.

6. The method according to claim 1, further including the step of providing a first code pattern on each of said removable labels that is unique for a type of said unit of use.

7. The method according to claim 6, further including the step of printing a second code pattern on said label image.

8. The method according to claim 7, further including the step of removing said removable label from said unit of use and placing said removable label onto said printout so that said first code pattern on said removable label lays in close proximity to said second code pattern on said label image.

9. The method according to claim 1, wherein said step of providing a central processing unit includes providing a central processing unit within said vending machine.

10. The method according to claim 1, wherein said step of providing a data reading unit includes providing said data reading unit within said vending machine.

11. The method according to claim 4, wherein said step of providing a printer includes providing said printer within said vending machine, whereby said printout extends from said vending machine when printed.

12. The method according to claim 1, further including the step of sensing if one of said units of use vends from said vending machine after said vending machine is activated.

13. A method of ensuring that a product vended from a vending machine is correct, said method comprising the steps of:

providing a printer that is connected to said vending machine;

filling said vending machine with products that are each identified with a unique code pattern;

activating said vending machine by entering a selection that corresponds to a chosen one of said products, therein receiving a vended product;

creating a printout on said printer that identifies said unique code pattern for said chosen one of said products; and determining if said unique code pattern identified on said printout is the same as said unique code pattern on said vended product.

14. The method according to claim 13, wherein said step of activating said vending machine includes the substeps of:

reading a first vending code to said vending machine that identifies one of said products contained in said vending machine;

providing a portable storage medium containing a second vending code that is paired to said first vending code;

bringing said portable storage medium to said vending machine;

reading said second vending code from said portable storage medium;

comparing said first vending code to said second vending code; and activating said vending machine if said first vending code matches said second vending code.

15. The method according to claim 13, further including creating a label image on said printout that contains graphical features.

16. The method according to claim 15, said unique code pattern contains graphical features, wherein said step of determining if said unique code pattern identified on said printout is the same as said unique code pattern on said vended product includes determining of said graphical features on said unique code pattern align with said graphical; features on said label image.

* * * * *